United States Patent [19]

Lutenegger et al.

[11] 4,411,160
[45] Oct. 25, 1983

[54] VANE MODULUS SOIL TESTER

[75] Inventors: Alan J. Lutenegger, Ames; John M. Pitt, Nevada, both of Iowa

[73] Assignee: Iowa State University Research Foundation, Inc., Ames, Iowa

[21] Appl. No.: 287,414

[22] Filed: Jul. 27, 1981

[51] Int. Cl.³ .............................................. G01N 3/24
[52] U.S. Cl. ....................................................... 73/843
[58] Field of Search ............... 73/843, 847, 84, 768, 73/775, 784

[56] References Cited

U.S. PATENT DOCUMENTS

| | | | |
|---|---|---|---|
| 2,907,204 | 10/1959 | Gibbs | 73/843 |
| 3,349,610 | 10/1967 | Noel . | |
| 3,443,123 | 5/1969 | Broise . | |
| 3,557,886 | 1/1971 | Cobbs . | |
| 3,561,259 | 2/1971 | Barendse . | |
| 4,091,661 | 5/1978 | Handy et al. | 73/784 |
| 4,157,528 | 6/1979 | Shuck et al. . | |

FOREIGN PATENT DOCUMENTS

| | | | |
|---|---|---|---|
| 452309 | 11/1948 | Canada | 73/775 |
| 525774 | 6/1977 | U.S.S.R. | 73/84 |
| 579581 | 11/1977 | U.S.S.R. | 73/84 |
| 709997 | 1/1980 | U.S.S.R. | 73/843 |

Primary Examiner—Steven L. Stephan
Assistant Examiner—David R. Schuster
Attorney, Agent, or Firm—Zarley, McKee, Thomte, Voorhees & Sease

[57] ABSTRACT

A vane modulus soil tester includes a multi-blade vane having a plurality of radially extended and circumferentially spaced-apart blades. The blades have cavities in which resistance-type strain gauges are carried for measuring stress on the face of the vane blades. At least strain gauges are situated so as to be "facing" each other.

A further embodiment may be provided with a series of independent levels of blades of different thicknesses whereby test values may be extrapolated to zero blade thickness conditions or the insitu value. A support base is provided for securely positioning a vane rod extended axially from the vane and for applying torque to the vane through the vane rod.

20 Claims, 6 Drawing Figures

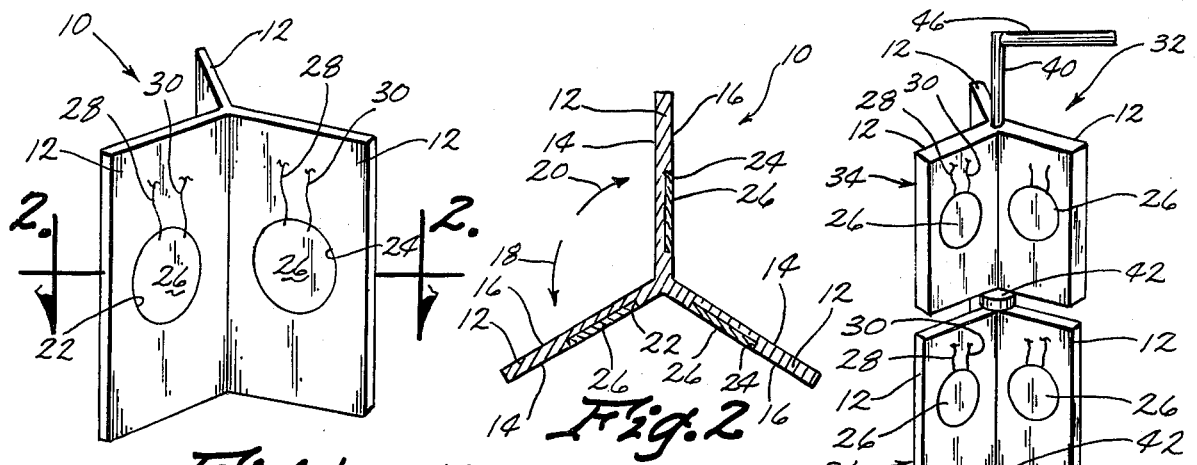
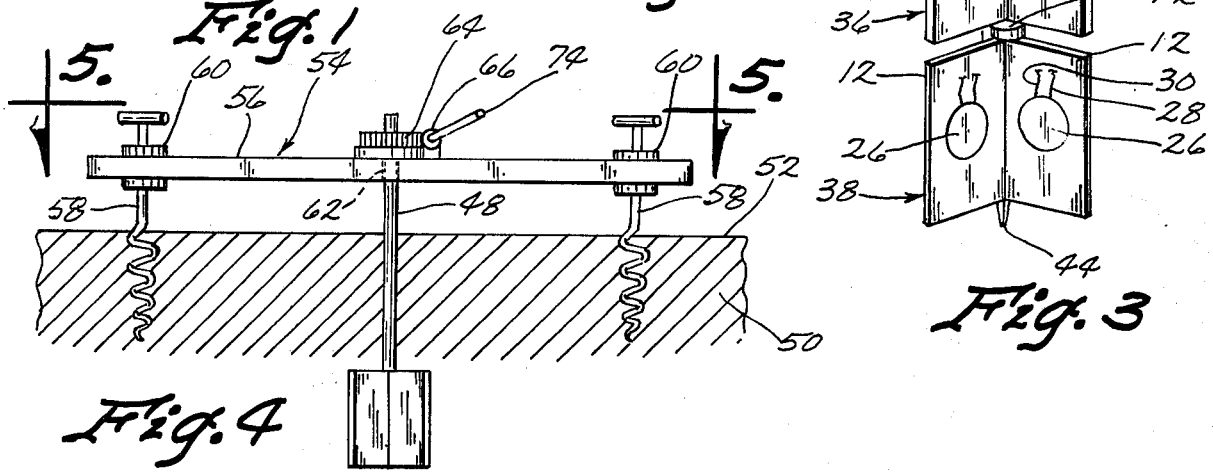
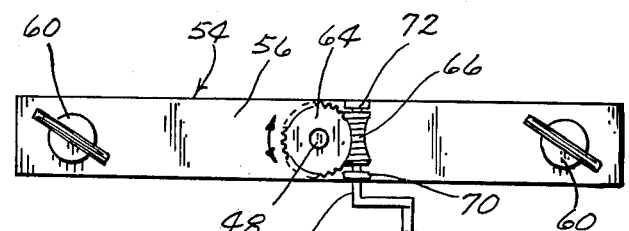
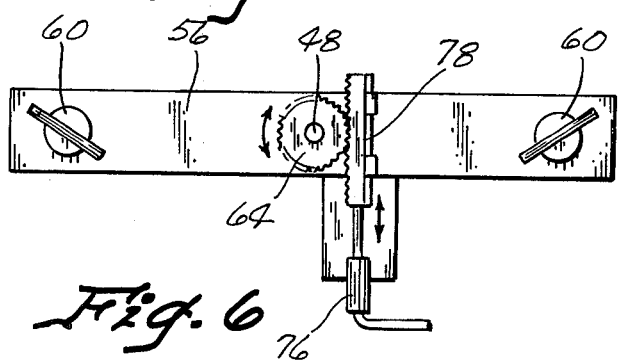

VANE MODULUS SOIL TESTER

BACKGROUND OF THE INVENTION

The present invention is directed generally to improved apparatus and techniques for measuring geotechnical properties of soil materials and more particularly to an improved multi-blade vane apparatus adapted for this purpose.

In the past, it was common to measure the geotechnical properties of soil materials in a laboratory by test procedures applied to a soil sample. Problems associated with common laboratory procedures, including unrealistic boundary conditions and disturbance as a result of sampling, have made the use of insitu methods more appealing. These methods have recently become a major interest of consulting engineers. The main problem with insitu testing has been the relatively high cost, which therefore limits its extended application.

Accordingly, a primary object of the present invention is to provide an improved apparatus and method for insitu measurement of geotechnical properties of soil materials.

Another object is to provide an improved multi-blade vane apparatus for the measurement of soil properties.

Another object is to provide a multi-blade vane apparatus including electrical pressure sensors for continuously monitoring stress while the vane is being inserted into the ground.

Another object is to provide a multi-blade vane apparatus wherein at least two blades have pressure sensors placed so as to face in opposite rotational directions.

Another object is to provide a multi-blade vane apparatus including a series of independent levels of blades of different thicknesses.

Another object is to provide an improved apparatus and method for obtaining discrete values of soil friction angle and cohesion.

A further object is to provide an improved method and apparatus for measuring the time-deformation characteristics or creep behavior of soils.

A further object is to provide an improved apparatus and method for measuring dynamic soil response for use in earthquake analysis and design of foundations for machine vibrations, etc.

Finally, a further object is to provide an improved multi-blade vane apparatus which is simple and rugged in construction, economical to manufacture and efficient in operation.

SUMMARY OF THE INVENTION

The vane modulus soil tester of the present invention enables the measurement of geotechnical properties of soil materials to be made economically and accurately with insitu methods. A multi-blade vane includes a plurality of radially extended and circumferentially spaced-apart blades. The blades carry resistance-type gauges for measuring the stress on the face of the vane blades. At least two blades have sensors placed in such a manner as to be "facing" each other, i.e. the sensors face in opposite rotational directions so that as torque is applied to the vane, stress on one sensor will increase while stress on the other sensor will decrease. Accurate, continuous, measurement of the stresses, applied torque and angular rotation of the vane, produces stress-strain data which can be used for calculation of the sheering modulus of soils.

An alternate multi-blade vane apparatus may be provided with a series of independent levels of blades of different thicknesses. By plotting the test values obtained at each level against the respective blade thickness, one can extrapolate to zero thickness for an estimate of the insitu value, i.e. no blade.

A support base is provided both for positioning the vane rod relative to the ground surface and for applying torque through the vane rod to the vane. Various manual and power torque application systems may be provided on the base structure to provide various testing conditions. Measurements taken from the multi-blade vane soil tester of the present invention under various conditions enables one to obtain discrete values of soil friction angle and cohesion. Furthermore, the time-deformation characteristics or creep behavior of soil may be measured as well as dynamic soil response.

DETAILED DESCRIPTION OF THE DRAWINGS

FIG. 1 is a perspective view of a multi-blade vane according to the invention;

FIG. 2 is a top sectional view, taken along line 2—2 in FIG. 1;

FIG. 3 is a perspective view of a multi-blade vane apparatus including a series of independent levels of blades of different thicknesses;

FIG. 4 is a partially sectional side elevational view of a support base in assembly relation with the multi-blade vane;

FIG. 5 is a top view of the support base as seen on line 5—5 in FIG. 4; and

FIG. 6 is a top view, similar to FIG. 5, of a support base showing an alternate torque application system.

DESCRIPTION OF THE PREFERRED EMBODIMENT

A multi-blade vane 10 for measuring the geotechnical properties of soil material is shown in FIG. 1. Vane 10 includes a plurality of upright thin walled blades 12, each having opposite surfaces 14 and 16 facing in respective opposite directions of rotation as indicated by arrows 18 and 20 in FIG. 2. The blades are supported in generally radially extended and circumferentially spaced-apart relation and preferably comprise integral parts of a unitary multi-blade vane 10 as shown in FIGS. 1 and 2.

Several of the blade surfaces 14 and 16 are provided with respective cavities 22 and 24 in which pressure sensors 26 are supported. The pressure sensors 26 may be electrical resistance-type strain gauges, each having a respective pair of lead wires 28 and 30. The sizes of the cavities 22 and 24 and strain gauges 26 are preferably related so that the strain gauges substantially fill the cavities and so that the exposed surfaces of the strain gauges are substantially co-planar with the adjacent exterior blade surface.

Referring to FIG. 3, a soil tester 32 is shown which includes three multi-blade vanes 34, 36 and 38, each of which includes three radially extended and circumferentially spaced-apart blades. As in the embodiment of vane 10, the exact number of blades is not critical to the present invention, however, three or four are acceptable. The vanes 34, 36 and 38 are each independently rotatably supported on a central vane rod 40 with bearings 42 therebetween. Rod 40 may be pointed at its lower end 44 and have a transverse lever 46 at its upper end to facilitate insertion of the soil tester 32 into the ground. The blades of each of the vanes 34, 36 and 38 are provided with pressure sensors similar to the arrangement described in connection with vane 10 of FIGS. 1 and 2.

Whereas the vanes 34, 36 and 38 are otherwise substantially similar, the thickness of the blades of vane 34 is greater than the thickness of the blades of vane 36 which, in turn, are thicker than the blades of vane 38. An important advantage of providing a series of independent levels of blades of different thicknesses is that it enables an engineer to make use of an extrapolation procedure. Specifically, test values obtained at each level would be plotted against the respective blade thickness and extrapolation to zero thickness gives an estimate of the insitu value, i.e. zero blade thickness.

In operation, vane 10 is secured to an axially extended vane rod 48 and pressed into the ground 50 below ground surface 52 as shown in FIG. 4. A support base 54 is provided for properly positioning the upper end of vane rod 48 and for applying torque thereto.

Support base 54 includes a transverse beam 56 having a pair of screw anchors 58 rotatably supported adjacent opposite ends thereof in bearings 60. Beam 56 is additionally provided with a central bore 62 for rotatably receiving the vane rod 48.

To apply torque to the vane rod 48, a gear 64 is fixed on an upper end of the vane rod for meshed engagement with a worm gear 66 which is fixed on a shaft 68 supported in bearings 70 and 72. An offset crank handle 74 on shaft 68 enables the worm gear 66, gear 64 and vane rod 48 to be manually rotated for the application of torque to the vane blades 12. It will be apparent that various other means are available for applying torque to the blades. Accordingly, the specific type of torque application system employed is not critical to the present invention.

Since the pressure sensor 26 detect stresses on the faces of the blades 12 electrically, the measurement of stress is continuously monitored while the vane is being inserted into the ground. Furthermore, since at least two of the blades 12 have sensors 26 arranged thereon in a manner so as to be "facing" one another, the stresses on the respective sensors 26 change when torque is applied to the vane rod 48. Specifically, in response to rotation in the direction of arrow 20 (FIG. 2) stress on the leading sensors 26 in cavities 24 increases, while stress on the trailing sensors 26 in cavities 22 decreases. Accurate and continuous measurement of the stresses, applied torque and angular rotation of the vane produces stress-strain data which can be used for calculation of the shearing modulus of soils.

An advantage of this invention over conventional vane shear in measuring insitu shear strength is obtaining discrete values of soil friction angle and cohesion. Since a measure of both shear stress and blade contact pressure is obtained simultaneously for different blade thicknesses, the required shear force for each thickness can be determined as previously described from torque measurements, giving a series of normal and shear stresses. These in turn can be plotted to produce the familiar Mohr-Coulomb failure envelope, from which cohesion and soil friction angle can be determined.

The soil testing method and apparatus of the present invention are further applicable for measuring the time-deformation characteristics or creep behavior of soils. This may be accomplished by applying a constant torque on the blade face, and measuring the resulting rotational deformation time. The constant force may be applied by substituting a fluid cylinder 76 and linearly movable rack gear 78 as shown in FIG. 6, for the worm gear 66 of the embodiment of FIG. 5. A pneumatic system utilizing a pressure regulator, for example, may be used to maintain a constant torque.

Another application of the present invention relates to the measurement of dynamic soil response for use in earthquake analysis and design of foundations for machine vibrations. This may be accomplished by applying repetitive or vibratory loading in the direction of shearing, at the torque head at the top of rod 48, and measuring the corresponding shear stress-displacement relationships of the vane. The application of repeated torque loading may be provided by a programmable servo mechanism, controlling either a load cylinder or an electromagnet.

By electrically connecting the resistance-type strain gauges 26 to appropriate read-out devices for measuring the stress on the face of the vane blades and applying a known torque to the vane rod 48, the stress-displacement relationship is given. By manipulation of the data, the following properties can thus be obtained quickly and economically: shear modulus (G), bulk modulus (K), undrained shear strength, insitu stress, and dynamic response. The application of these measurements is almost unlimited and includes a variety of common design practices. Input into finite element analysis, use of at rest stress ratio (K subzero), bearing capacity and earthquake analysis are among the basic uses.

Thus there has been shown and described a vane modulus soil testing system which accomplishes at least all of the stated objects.

We claim:

1. A vane modulus soil tester, comprising,
    a plurality of generally thin blades having opposite surfaces,
    means for supporting said blades in generally radially extended and circumferentially spaced-apart relation,
    at least two pressure sensors each being operative to measure pressure changes on a single surface of a blade, one pressure sensor being mounted on one blade and facing in one rotational direction and the other being mounted on another blade and facing in the opposite rotational direction, and
    power means for rotating said blades in opposite directions.

2. The soil tester of claim 1 wherein said one blade and said another blade are adjacent blades and said pressure sensors are mounted on blade surfaces which face one another.

3. The soil tester of claim 1 wherein said pressure sensors include a resistance-type strain gauge.

4. The soil tester of claim 1 wherein said pressure sensors are supported in cavities in said blades whereby the exterior surface of each pressure sensor is substantially co-planar with the adjacent exterior blade surface.

5. The soil tester of claim 1 further comprising a plurality of levels of blades including an uppermost level and at least one lower level, the blades of each lower level having a thickness which is less than the thickness of the blades in the next adjacent higher level, the blades of different levels having different thicknesses.

6. The soil tester of claim 5 wherein all of the blades on each level are of uniform thickness.

7. The soil tester of claim 5 further comprising means for supporting said levels of blades so that the blades of one level are rotatable in unison independently of the rotation of blades of different levels.

8. The soil tester of claim 1 said means for supporting said blades further comprising an elongated vane rod connected to said blades and extended axially therefrom.

9. The soil tester of claim 8 wherein said power means for rotating said vane rod is operative to apply a constant torque thereto.

10. The soil tester of claim 9 wherein said power means for rotating said vane rod comprises a support base adapted to be anchored to the ground and coacting gear means operatively connected to said vane rod and base structure for rotation of said vane rod in response to rotation of said coacting gear means.

11. The soil tester of claim 10 further comprising a fluid actuated power cylinder operatively connected to said coacting gear means and operative to apply constant torque to said vane rod.

12. The soil tester of claim 1 wherein said plurality of thin blades comprises an integral multi-blade vane.

13. A method for insitu measurement of geotechnical properties of soil, comprising,
providing a multi-blade vane wherein said blades extend radially outwardly in circumferentially spaced-apart relation, each blade having one surface facing in a first rotational direction and an opposite surface facing in the opposite rotational direction,
inserting said multi-blade vane into the ground,
applying torque to said inserted vane,
detecting stress on said one surface of a respective blade,
and
detecting stress on said opposite surface of another respective blade.

14. The method of claim 13 wherein said step of detecting stress comprises placing a resistance-type strain gauge on the respective blade surface and electrically monitoring the output signals from said strain gauge.

15. The method of claim 14 further comprising continuously monitoring said strain gauges while said vane is being inserted into the ground.

16. The method of claim 13 wherein said step of applying torque comprises applying torque at the surface of the ground, and communicating said torque from the surface of the ground to said inserted vane.

17. The method of claim 15 further comprising providing vertically spaced levels of blades of different thicknesses, obtaining test values at each level, plotting said test values against blade thickness, and extrapolating to zero blade thickness thereby to determine an estimate of the insitu stress value.

18. The method of claim 13 further comprising measuring time deformation characteristics of the soil by applying a constant torque to the vane and measuring the resulting rotational deformation of the vane.

19. The method of claim 15 wherein the step of applying a constant torque is accomplished by operatively connecting a fluid cylinder to said vane.

20. The method of claim 13 further comprising applying repeated torque loading to said vane and measuring the corresponding shear stress-displacement relationships of the vane.

* * * * *